(12) United States Patent
Chukwu

(10) Patent No.: US 8,226,996 B2
(45) Date of Patent: Jul. 24, 2012

(54) BIOACTIVE RAW VEGETABLES

(75) Inventor: Uchenna N. Chukwu, Minnetonka, MN (US)

(73) Assignee: Uchenna N. Chukwu, Minnetonka, MN (US)

( * ) Notice: Subject to any disclaimer, the term of this patent is extended or adjusted under 35 U.S.C. 154(b) by 110 days.

(21) Appl. No.: 12/655,422

(22) Filed: Dec. 29, 2009

(65) Prior Publication Data

US 2010/0112134 A1 May 6, 2010

Related U.S. Application Data

(63) Continuation-in-part of application No. PCT/IB2008/001659, filed on Jun. 25, 2008, and a continuation-in-part of application No. 11/881,539, filed on Jul. 27, 2007, which is a continuation-in-part of application No. 10/619,403, filed on Jul. 14, 2003, now Pat. No. 7,407,678, which is a continuation-in-part of application No. 09/495,960, filed on Feb. 2, 2000, now abandoned, which is a continuation-in-part of application No. 09/196,844, filed on Nov. 20, 1998, now Pat. No. 6,033,692.

(51) Int. Cl.
*A23L 1/30* (2006.01)
(52) U.S. Cl. ............................. 426/63; 426/61; 426/64
(58) Field of Classification Search .................... 426/61, 426/63, 64
See application file for complete search history.

(56) References Cited

U.S. PATENT DOCUMENTS 3,632,346 A * 1/1972 Sherba ........................... 426/46
5,989,600 A * 11/1999 Nielsen et al. ................. 426/52

OTHER PUBLICATIONS

JP-61-162185-1986—English Abstract—pp. 6-7.*

* cited by examiner

*Primary Examiner* — Callie Shosho
*Assistant Examiner* — Hamid R Badr

(57) ABSTRACT

The present invention includes bioactive coated raw vegetables that include bioactive compositions coated onto the raw vegetables, such that the bioactive compositions are effective to degrade raffinose, stachyose and verbascose in the raw vegetables when the raw vegetables are placed in optimal pH and temperature conditions. The present invention also includes methods of forming bioactive coated raw vegetables.

21 Claims, No Drawings

BIOACTIVE RAW VEGETABLES

CROSS-REFERENCE TO RELATED APPLICATION(S)

This application is a continuation-in-part application of International Application PCT/IB2008/001659 filed on Jun. 25, 2008, entitled "BIOACTIVE RAW VEGETABLES" by Chi's Research Corporation, which designated the United States and which claimed priority from U.S. Serial Application Number 60/947,387, entitled "Bioactive Coated Raw Legumes" by Uchenna N. Chukwu filed Jun. 29, 2007 and U.S. Ser. application No. 11/881,539 filed Jul. 27, 2007 entitled "Bioactive Raw Vegetables" by Uchenna N. Chukwu all of which are incorporated herein in their entirety. This application is also a continuation-in-part application of U.S. Ser. application No. 11/881,539 filed Jul. 27, 2007 entitled "Bioactive Raw Vegetables" by Uchenna N. Chukwu which is incorporated herein in its entirety.

BACKGROUND OF THE INVENTION

During the last several years, consumer interest in eating foods that are nutritionally balanced with an adequate source of protein, fat, carbohydrates, fiber, vitamins and minerals has increased. Growing concern over chronic diseases, such as cancer, diabetes and heart disease have motivated consumers to seek foods for consumption that are effective in treating chronic diseases while promoting a healthier lifestyle.

Consumption of vegetables having phytochemicals may prove challenging to individuals as vegetables contain anti-nutritional components, such as indigestible sugars, enzyme inhibitors, nutrient-binding substances or toxic compounds. Heat and/or pressure processing of vegetables to eliminate anti-nutritional components in the vegetable prior to consumption are the traditional approach used by food manufacturers. However, heat and/or pressure processing may eliminate most, if not all phytochemicals during the manufacturing process. While certain plant materials have been degraded or modified with one or more enzymes to form nutritional plant foods, enzymes are typically applied to the plant material when the plant material is in the form of a slurry rather than in whole form which results in modification of the plant material and loss in nutrient status. In addition, enzymes like cellulase and xylanase have been sprayed onto raw plant materials having a low moisture content of less than about 15 weight percent to form enzyme coated plant materials. However, this technique is problematic since enzyme application results in undesirable enzymatic degradation and/or premature deactivation of enzymatic activity.

SUMMARY OF THE INVENTION

The present invention includes a method of forming a bioactive coated raw legume by applying a liquid binder to a raw legume to form a sticky raw legume followed by applying a granular bioactive composition comprising at least one enzyme to the sticky raw legume to form the bioactive coated raw legume.

The present invention further includes a method of forming a bioactive coated raw vegetable by coating a raw whole vegetable with a slurry comprising a binder and a bioactive composition to form a slurry-coated raw vegetable, such that the bioactive composition is effective to degrade raffinose, stachyose, verbascose followed by curing the slurry to form the bioactive coated raw vegetable.

The present invention also includes a bioactive coated raw legume that includes a raw whole legume having a moisture content of less than about 40 weight percent, based on the total weight of the legume and a binder coated onto the raw legume, such that the binder has a concentration of more than about 0.0001 weight percent, based on a total weight of the raw legume. The bioactive coated raw legume also contains a bioactive composition mixed with the binder. The bioactive composition contains at least one enzyme that is effective to degrade raffinose, stachyose, verbascose and has a concentration of at least about 0.0001% weight percent, based on the total weight of the raw legume.

The present invention also includes bioactive coated raw vegetables that includes raw vegetables with a moisture content of less than about 40 weight percent, based on the total weight of the raw vegetable coated with a binder and a bioactive composition such that the binder and bioactive composition have a concentration of more than about 0.01 weight percent, based on a total weight of the raw vegetable. The bioactive composition includes at least one enzyme that is effective to break down raffinose, stachyose, and/or verbascose.

DETAILED DESCRIPTION

The present invention includes bioactive raw whole vegetables that have been coated or covered with bioactive compositions that contain enzymes which retain their activity after the coating process and are effective to degrade to raffinose, stachyose and/or verbascose when the bioactive raw whole vegetables are placed in optimum temperature, solvent (water) and pH conditions. The present invention further includes methods of forming the bioactive raw whole vegetable by coating dry clean raw whole vegetables with a bioactive composition that is adhered to the raw vegetable with a binder. After coating the raw vegetables with bioactive compositions, the coated raw vegetables are typically dried to remove any surface moisture or the coating is cured, hardened and/or solidified to ensure that the bioactive coating is retained on the raw vegetables. As used herein, the term "bioactive raw whole vegetables" refers to raw whole vegetables that include a bioactive coating containing one or more enzymes capable of enzymatic activity when placed in optimum temperature, pH and solvent conditions. The term "bioactive raw vegetables" also refers to raw whole vegetables that include a bioactive coating containing at least one vitamin and/or mineral without the presence of an enzyme.

In use, when the bioactive raw whole vegetables are placed in a sufficient amount of an aqueous composition under normal atmospheric pressures and at a temperature that ranges from about 70° F. to about 212° F., and preferably at a temperature that ranges from about 90° F. to about 150° F., the bioactive coating leaches into or dissolves into the aqueous composition and the ingredients in the bioactive coating disperse and/or dissolve in the aqueous composition. When the aqueous composition is brought to a pH range of about 2 to about 8, and preferably a pH range of about 3 to about 7, the enzymes in the bioactive coating are capable of hydrating, tenderizing, degrading, modifying and/or reducing the raffinose, stachyose, and verbascose levels present in the raw whole vegetable to form a vegetable product. The ratio of the raw vegetable to aqueous composition that is used to initiate enzyme activity typically ranges from 1:1 to 1:10 (vegetable: aqueous composition) or 1:1 to 1:5 depending on the type of raw vegetable and bioactive composition.

Exemplary raw whole vegetables that are suitable for use in the present invention include dry edible beans, legumes, pulses, grains, or any other raw whole vegetable having a moisture content of less than about 40 weight percent, and in particular, less than about 30 weight percent. In addition, the raw vegetable is preferably a whole raw vegetable. By "whole" is meant that the raw vegetable has not been subjected to techniques like maceration, pulverization, grating, grinding or the like. While raw whole vegetables preferably contain a moisture content of less than about 40 weight percent, raw whole vegetables that have more than 40 weight percent may also be coated with the bioactive compositions when practicing the present invention.

As used herein, the term "raw" refers to vegetable(s) that are uncooked, un-boiled, dry, edible, as being in a natural condition, not processed or any combination of any of these. It is also to be understood that the term "whole raw vegetable" is meant to encompass broken a raw vegetable that (1) has a first outer layer that is in adhesive contact with a second layer or inner portion that is exposed. For example, in the manufacture of refried beans, broken portions of whole beans still contain a seed coat and exposed cotyledons.

The raw whole vegetables may be characterized in terms of piece counts and size. For example, raw vegetables such as legumes, grains, dry edible beans, soybeans or other raw whole vegetables in particulate form that typically have piece counts that range from about 50 to about 15,000 per pound are suitable for use in the present invention. Preferably, the raw whole vegetables have piece counts that range from about 50 to about 2500 per pound. Furthermore, the raw whole vegetables may have sizes that range from about 0.1 millimeters (mm) to about 20 mm when coating with bioactive compositions in accordance with the present invention. Preferably, the vegetables have sizes that range from about 0.5 mm to about 15 mm. For example, pinto beans have a piece size of about 10 mm to about 12 mm while navy beans have a piece size of about 3 mm to about 4 mm.

In addition, the raw whole vegetables that may be used to practice the present invention may also be characterized in terms of piece weight. By "piece weight" is meant the weight in grams of one (single) raw whole vegetable in particulate form. In general, piece weights of raw whole vegetables ranges from 0.01 grams to 15 grams and preferably, 0.01 grams to 10 grams.

Raw whole vegetables that are suitable for use in the present invention may be characterized as vegetables that (1) require presoaking, (2) require cooking and/or processing to render the raw whole vegetable fit for human consumption and/or (3) contain at least about 0.1 weight percent, and preferably at least about 0.5 weight percent oligosaccharide sugars. By "oligosaccharide sugars" as used herein, is meant raffinose, stachyose, verbascose sugars or any combination of any of these. For example, raw whole vegetables that contain about 0.5 weight percent to about 6 weight percent oligosaccharide sugars, based on the total weight of the raw whole vegetable are considered optimal in the present invention even though raw whole vegetables that have less than about 0.5 weight percent or more than about 6 weight percent oligosaccharide sugars, based on the total weight of the raw whole vegetable can also be coated in accordance with the present invention.

For purposes of this invention, "dry clean" vegetables are typically coated when practicing the present invention. As used herein, "dry clean" refers to a vegetable from the field in which the foreign material adhered to or associated with the vegetable is removed before undergoing any of the method steps of the present invention hereinbelow, i.e., prior to undergoing any significant soaking except that which is used in the cleaning step. Unless indicated to the contrary, the term "dry vegetable" refers to a vegetable having the moisture content of a vegetable naturally found in the field. Furthermore, it is preferred that the vegetable be cleaned prior to coating with the bioactive compositions as cleaning the vegetables after the coating has deposited will cause the coating to be removed to some degree. Therefore, cleaning of the vegetables is permissible and in some cases preferred in order to remove surface dirt present on the raw vegetables.

In one embodiment, raw whole legumes are cleaned with a sufficient amount of water for a sufficient period of time that produces legumes having a moisture content in the range from about 15% to about 30% by weight, using techniques known in the art. The dry legume can be contacted with the water source used in the cleaning step by any method known to the skilled artisan. Examples of useful methods include, but are not limited to, spraying, immersion, repeated dipping, misting, floating, diffusion, steam condensing or combination thereof, with immersion being the most preferred. This cleaning step, if utilized is effected at ambient temperatures. Typically, raw vegetables that have been cleaned are also dried to eliminate most, if not all surface moisture and to optionally reduce the overall moisture content.

As used herein, the term "legume" refers to a vegetable belonging to the family Leguminosae. It is characterized as having a dry, dehiscent fruit derived from a single, simple pistil. When mature, it splits along both dorsal and ventral sutures into two valves. The family Leguminosae characteristically contains a single row of seeds attached along the lower or ventral suture of the fruit. Ordinarily, the legume seeds used for the present invention are the usual dry seeds available in commerce. For example, in the case of beans, these products are referred to as dry beans because the product includes only the mature seeds, the pods having been removed. Examples of legume seeds useful in the present invention include seeds of the genus *Phaseolus*, including, without limitation, the common beans such as large white or Great Northern, small white, pinto, red kidney, black, calico, pink cranberry, red mexican, brown, bayo, lima, navy and the like; the genus *Pisum*, including, without limitation, smooth and wrinkled peas and yellow or green varieties and the like; the genus *Vigna*, including the black eye beans (or black eye peas as they are sometimes termed), cowpeas, purple hull peas, cream peas, crowder peas, field peas and the like; the genus *Lens*, including without limitation, lentils; the genus *Cicer*, including, without limitation, garbanzo beans and chick peas; the genus *Soja*, including, without limitation, soybeans; and the like. Other examples of legume seeds useful in the present invention include red beans, yellow-eye beans, azuki beans, mung beans, tepary beans, and fava beans and the like. In addition, the term "legume" is meant to encompass the word "pulse" (plural "pulses") generally used for this class of edible seeds in most English-speaking countries.

Furthermore, the term "legume" used herein refers to both legumes rich in protein and starch and legumes rich in oil, also referred to as oleaginous legumes. By "legumes rich in protein and starch" is meant whole legumes having a protein content of from 15 to 48% or more and a starch content of from 35 to 75% on a dry matter basis, but most commonly having a protein content of from 20 to 36% and a starch content of from 55 to 70%. Such legumes have been distinguished from oleaginous seeds by having a lipid content only of from 0.5 to 5.0%, and more commonly of from 1.0 to 2.5%. Legumes derived from legumes of the genus *Lupinus* may also be used in the process according to this invention since such legumes are rich in protein, having a protein content of from 40 to 50%, although they may contain somewhat lower amounts of starch and higher amounts of oil than other legumes. Other suitable raw whole vegetables includes grains such as bulgur, amaranth, millet, rice, brown rice, sorghum, corn, rye, triticale, quinoa or any combination of any of these.

To prepare bioactive raw vegetables, one or more raw whole vegetables are coated or covered with a quantity of a binder to adhere the bioactive composition to the raw whole vegetable. The binder that is used preferably (1) does not promote enzymatic degradation during the coating process, (2) helps to maintain the desired enzymatic activity when desirably exposed to the proper pH, temperature and solvent (water) conditions, (3) can be easily applied to the raw whole vegetable, (4) easily sticks to the raw whole vegetable and the bioactive composition, and (5) does not negatively affect the organoleptic properties of the raw whole vegetables or the raw whole vegetables after being subjected to enzymatic degradation by the bioactive composition.

The binder may be supplied in a paste, fluid, solid, liquid, mist, vapor, or in granular form. Preferably, the form that is selected is capable of adhering the binder and bioactive composition to the raw whole vegetable. Still more preferably, the binder is liquid or fluid form when practicing the present invention.

The binder is typically at a concentration that is effective in adhering the bioactive coating to the raw whole vegetables. Hence, the particular binder usage level depends upon a variety of factors such as the desired textural properties in the finished product, storage conditions, coating conditions, raw whole vegetable and bioactive compositions.

In general, good results can be obtained when the binder has a concentration of about 0.0001 weight percent to about 10 weight percent, based on the total weight of the raw whole vegetables when practicing the present invention. For example, when the liquid binder is applied separately from the bioactive composition, the binder is at a concentration of about 0.5 to about 5 weight percent, based on the total weight of the raw whole vegetable. In another example, when both the liquid binder and the bioactive composition are mixed to form a slurry, the binder is at a concentration that ranges from about 3 weight percent to about 10 weight percent, based on the total weight of the raw whole vegetable.

The art is replete with suitable binding agents and the skilled artisan will have no difficulty in selecting suitable binding(s) for use herein. The binder can be oil-based, water-based, or a combination of both water- and oil-based as long as the binder is not capable of causing undesirable enzymatic degradation during the coating process. Oil-based binders that are suitable for use in the present invention may be characterized as oils and/or fats that have a melting point of more than about 90° F. and are generally solid at a room temperature of about 70° F. Furthermore, suitable oil-based binders for the present invention are preferably stable to pH ranges of about 2 to about 7 so that premature degradation of the binder is avoided.

The oil-based binder is typically melted to form a liquid by heating to more than about 90° F. prior to application to raw whole vegetables. For example, the oil-based binders of the present invention are melted by heating to a temperature of about 100° F. to about 135° F. during coating of raw edible beans to attain optimal coverage of the surface by the liquefied oil-based binder. In addition, including oil-based binders with a melting point of between about 90° F. and about 140° F. in the present invention is preferred so that the bioactive coating does not easily melt off the raw whole vegetables during storage in conditions above 90° F.

Fats and/or oils that have a melting point of more than about 90° F. include partially hydrogenated palm kernel, soybean, cottonseed, corn, canola, peanut, palm, babassu, sunflower, and/or safflower oils; fully hydrogenated palm kernel, canola, soybean, cottonseed oil; blends of partially hydrogenated and fully hydrogenated palm kernel, soybean, canola, cottonseed, corn, peanut, palm, babassu, sunflower, and/or safflower oils; mono-, di- and triglycerides; other food-grade paraffin-based waxes, food-grade petroleum waxes, carnuba wax, bran wax, tallow, shellac, or beeswax; or any combination of any of these. Some non-exhaustive examples of oil-based binders include Olympic® series palm kernel oils and partially hydrogenated palm kernel oils (100, 200, 300, 400) that are available from Cargill (Minnetonka, Minn.); Encore® palm kernel, and partially hydrogenated palm kernel oils (100, 100-F, 200, 300, 500, 600 and 800), Regal® partially hydrogenated palm kernel oils (HB-C-92, HB-E-95, HB-G-102, HB+108, HB-K-112, HB-M-100) and Regal® topping oils; veggie waxes, such as Naturewax® candle base stock S-113 that is also available from Cargill (Minnetonka, Minn.); or RBHD IE PKO-74-550-0 palm kernel oil that is available from ADM (Decatur, Ill.).

Fats and/or oils that have melting points of less than about 90° F. are also considered suitable for practicing the present invention as long as the oil-based binder is capable of adhering the bioactive composition to the surface of the raw whole vegetable in a manner that minimizes most, if not all, flaking off (removal) of the bioactive composition after coating. When fats and/or oils that have melting points of less than about 90° F. are used as the oil-based binder, a wax may be employed to give structure to the binder. Exemplary waxes have been described above.

Water-based binders are generally applied in dissolved or dispersed in liquid form. Suitable ingredients that may be used to form the water-based binder include solutions and/or slurries of gums, such as guar, pectin, carrageenan, xanthan, acacia, locust bean, gum tragacanth, gellan, carboxyl methylcellulose; proteins, such as gelatin, zein, soy protein, egg whites; starches such as pregelatinized starches, modified starches, sweetening agents like sucrose, dextrose, corn syrup, honey, fruit juices, food grade polyvinyl alcohol, polyvinyl pyrrolidone, polyethylene glycol, carboxylated styrene, styrene-maleic acid condensates; other natural and synthetic resins and polymeric materials; or any combination of any of these.

The water-based binders typically have a solids concentration of more than about 10 weight percent, based on the total weight of the water-based binder when practicing the present invention. During coating of raw legumes, the visual attributes are important factors that influence quality in the mind of the U.S. consumer. Therefore, liquid water-based binders that have more than 10 weight percent, and in particular more than 20 weight percent are considered beneficial during coating of raw legumes and grains as the higher solids concentrations minimizes undesirable seed coat modifications. Suitable water-based binders that can be used in the present invention include Dry Lock adhesive that is available from Specialty Products & Technology (Minnetonka, Minn.) and N-Tack waxy corn starch that is available from National Starch and Chemical Company (Bridgewater, N.J.).

The liquid binder is generally applied at a concentration of less than about 10 weight percent, based on the total weight of the raw vegetable. For example, when coating raw whole soybeans, the liquid binder is applied at a concentration of about 5 weight percent or less. In another example, the liquid binder is sprayed onto raw pinto beans at a concentration that ranges from about 0.5 weight percent to about 2 weight percent, based on the total weight of the raw whole pinto beans.

In addition, the liquid binder is typically applied to the raw whole vegetables at a temperature that ranges from 90° F. to 140° F. when practicing the present invention. For example, when coating raw great northern beans, an oil-based binder is applied at a temperature that ranges from about 90° F. to 140° F. Temperatures higher than 140° F. are to be avoided as premature deactivation of the bioactive composition may occur. In another example, when coating raw black beans, a water-based liquid binder is applied at a temperature of about 90° F. to about 130° F.

The bioactive composition may be supplied in liquid, as a piste, powder, mist, vapor, liquid or in solid form. Preferably, the form that is selected depends on how the bioactive composition is coated onto the raw whole vegetables. For example, if the bioactive composition is to be applied to the raw whole vegetables separately from the binder, then the bioactive composition is preferably applied as a powder or in granular form. If the bioactive composition is to be included as part of the binder to form a slurry that is used to coat the raw whole vegetables, then the bioactive composition can be supplied in any form so long as the bioactive composition is suitably dispersed or dissolved in the binder.

The concentration of the bioactive composition that is used to coat raw whole vegetables may vary depending on the (1) coating conditions, (2) coating equipment, (3) storage conditions of finished coated raw whole vegetable, (4) the binder concentration, (5) the ingredients used to form the binder, (6) the raw whole vegetable, (7) the desired degree of enzyme modification/processing, (8) the amount of time available to enzymatically degrade the raw whole vegetable, (9) the conditions that will be used to activate the enzyme component, and /or (10) other components and/or ingredients present in the bioactive composition. In general, the bioactive composition has a concentration that ranges from about 0.0001 weight percent to about 10 weight percent, based on the total weight of the raw whole vegetable when practicing the present invention. Preferably, the bioactive composition ranges from about 0.01 weight percent to about 2 weight percent, based on the total weight of the raw vegetable.

The bioactive composition may include (1) an enzyme component only and/or (2) may optionally include a pH-modifying component, an emulsifier component and other additional ingredients that aid the coating process and/or modify the chemical and nutritional properties of the raw whole vegetables when practicing the present invention.

The enzyme component contains one or more enzymes. Preferably, the enzymes do not degrade target substrates in the raw whole vegetables during the coating process. Furthermore, the enzymes generally remain active i.e., are capable of enzymatic activity (degrading target substrates) after the coating process and upon immersion in or contact with a sufficient amount of water under optimum pH and temperature conditions that initiate enzymatic activity. As used herein, the term "enzyme" means any complex protein produced by a living cell that is capable of at least catalyzing a specific biochemical reaction on one or more target substrates. The term "enzyme" is also meant to encompass any complex protein' capable of catalyzing a specific biochemical reaction that is substantially free of any microorganism.

Furthermore, the enzyme component is not meant to include the use of microorganisms to hydrolyze and/or degrade raw vegetables in accordance with the present invention. The application of microorganisms that produces carbohydrases and other enzymes to process raw vegetables is commonly referred to as microbial fermentation. Additionally, although microbial fermentation may involve some degree of hydrolysis, microbial fermentation is known to further transform sugar components like pentoses or hexoses into organic acids that increases the acidity, reduces the pH, and alters the texture and taste of the fermented vegetable. In contrast, the present invention uses enzymes that are substantially free of microorganisms to form the bioactive compositions.

As disclosed in U.S. Pat. No. 6,033,692, raw whole vegetables, such as raw dry edible beans can be enzymatically modified or processed using aqueous enzyme compositions that include carbohydrases, proteases, lipases and other enzymes. Aqueous enzyme compositions have also been shown to hydrate, tenderize, degrade, and/or modify raw whole vegetables as disclosed in Serial Application Nos. 10/619,403, 60/820,499, 60/863,388, 09/495,960, 60/947, 387, 11/881,539 and PCT Application No. US03/41646 which are incorporated herein in their entirety.

The enzyme component preferably includes one or more enzymes that are effective to degrade raffinose, stachyose and verbascose sugars in raw whole vegetables when practicing the present invention. Therefore, the enzyme component preferably includes carbohydrases, such as cellulase, hemicellulase, pectinase, amylase, alpha-galactosidase and an endoprotease, or combinations of any of these, which have been shown to eliminate up to 100% of raffinose and stachyose in dry edible beans and green leafy vegetables after immersion in or contact with aqueous enzyme compositions that include the above mentioned enzymes. To degrade raffinose, stachyose and verbascose in oleaginous legumes and other raw whole vegetables with an appreciable lipid content, the enzyme component generally includes cellulase, hemicellulase, pectinase, amylase, lipase alpha-galactosidase, a protease, or any combinations of any of these to eliminate up to 100% of raffinose and stachyose. By "appreciable lipid content" is meant vegetables that have a lipid or fat content of more than 0.5 weight percent, and preferably more than 1 weight percent, based on the total weight of the raw whole vegetable.

The oligosaccharide sugars in the vegetable product produced after contacting the bioactive raw whole vegetables with sufficient water under optimal temperature and pH conditions, is typically less than about 0.5% by weight of the vegetable product, and less than 0.05% by weight of the vegetable product and often times about 0% by weight. Similarly, the concentration of the verbascose and raffinose is about 0% by weight of the vegetable product and that the concentration of stachyose is less than about 0.5% by weight of the vegetable product and often times less than 0.05% by weight of the vegetable product. Alternatively, should the goal of enzyme modification be to tenderize, improve hydration or facilitate cooking/processing of the raw whole vegetable, rather than reduction of oligosaccharide sugars, then the enzyme component would include tenderizing enzymes such as cellulase, hemicellulase, amylase, pectinase, proteases, lipases or any combination of any of these.

In the present invention, active enzyme degradation during the coating process is preferably avoided for several reasons. The first reason is that the bioactive raw whole vegetables are expected to undergo enzyme degradation after the coating process as a result of exposure to a sufficient amount of water under pH and temperature conditions that promote enzymatic degradation therefore, retention of maximum enzyme activity is necessary. The second reason is premature enzyme activity during the coating process can result in partial hydrolysis of the raw whole vegetables which often affects organoleptic qualities of the coated raw whole vegetables. A third reason is that enzyme degradation during the coating process could also result in reduced enzyme activity in a manner that could ultimately limit, most if not all enzyme degradation when desired.

Enzyme degradation is avoided during the coating process by (1) encapsulating the bioactive composition in a matrix that prevents the enzymes from coming into contact with any target substrate in the raw whole vegetable, or (2) avoiding exposure to conditions, such as sufficient water, temperature and/or pH that foster enzyme degradation, and/or (3) optionally using a binder that does not allow enzyme degradation during the coating process.

The enzyme component can be included as part of the bioactive composition as a solid, concentrate, paste, liquid or in granular form. Preferably, the enzyme component is included as part of the bioactive composition in granular form when the bioactive composition is in granular form and is applied to the raw vegetables separately from the binder. Alternatively, the enzyme component can be included as part of the binder in the same or different form as the binder. For example, when the binder is in liquid form, the enzyme component can be added as a solid, concentrate, paste, liquid or in granular form that is mixed in with the liquid binder.

Preferably, the concentration of the enzyme component is an amount that is effective to tenderize, degrade, hydrolyze, modify, such as by reducing the raffinose, stachyose and verbascose in the raw vegetable after placing the enzyme-coated raw whole vegetables in sufficient water, temperature and pH conditions. Furthermore, it is to be understood that the concentration of the enzymes may vary depending on (1) activity of the enzymes, (2) enzyme processing time, (3) enzyme processing conditions, (4) desired degree of hydrolysis, (5) binder ingredients and concentration used, (6) raw whole vegetable, (7) coating conditions and equipment, and/or (8) storage conditions of the finished coated raw whole vegetable.

As disclosed in Serial Application Nos. 60/820,499, 60/863,388, 10/619,403, 09/495,960, 60/947,387, 11/881,539 and U.S. Pat. No. 6,033,692, the enzyme component generally ranges from about 0.0001 weight percent to about 10 weight percent, based on the total weight of the raw vegetable. When the enzyme component is included in granular form, the enzyme component concentration ranges from about 0.01 weight percent to about 1 weight percent, based on the total weight of the raw vegetable. When the enzyme component is included as a paste, liquid, mist, slurry, or in vapor form, the concentration generally ranges from about 0.05 weight percent to about 5 weight percent.

In an alternate embodiment, the enzyme component may be encapsulated to minimize enzymatic degradation during the coating process particularly if (1) a water-based binder and/or (2) a pH-modifying component is also included during formation of the bioactive coating. Encapsulated enzymes may also improve the stability of the coated vegetable during storage. Granular (powdered) enzymes may be characterized in terms of the particle size. Preferably, enzymes, both encapsulated or not, have a particle size of about 1 to 1000 microns, preferably about 1 to 250 microns and for best results about 5 to 100 microns when practicing the present invention.

Some non-exhaustive examples of cellulases or carbohydrases that can be used in the present invention include Cellulase AP and/or Cellulase T (Amano Enzymes USA, Chicago, Ill.); Enzeco cellulase CEP and/or Enzeco cellulase CE-2 (Enzyme Development Corporation (EDC), New York, N.Y.); Cellulase 4000 or Crystalzyme Cran (Valley Research Inc., South Bend, Ind.); Viscozyme L, or Cellubrix, Peelzym, Gamanase 1.0L (Novozymes, Franidinton, N.C.); Multifect cellulases (Danisco, Calif.); or Rapidase tropical cloud, Cytolase PC15, Cytolase CL (Gist Brocades, N.J.).

Some non-exhaustive examples of suitable lipases for the present invention include Yeast lipase 200,000 FIP/GM and/or Lipase 150,000 FIP/GM (Bio-cat, Troy, Va.); Lipase F-AP15, Lipase M Amano 10, Lipase G Amano 50, Lipase F Amano, Lipase A Amano 12, Lipase R. Amano, Lipase AY Amano 30 (Amano Enzymes USA); Fungal lipase 8000 (Valley Research, Inc); or Enzeco lipase concentrate (EDC). Some non-exhaustive examples of suitable pectinases include pectinase 500,000 AJDU/GM or pectinase 3,500 ENDO-PG/GM (Bio-cat), pectinase p-II (Amano Enzymes USA); or Multifect pectinase FE (Danisco).

Suitable amylases for the present invention include Enzeco fungal amylase (EDC), amylase DS, Amylase S Amano, Amylase THS Amano, and Amylase AY Amano (Amano Enzymes USA).

Suitable alpha-galactosidases include α-d-galactosidase or α-d-galactosidase DS (Amano Enzymes USA), Enzeco alpha-galactosidase concentrate (EDC); and Validase AGS (Valley Research, Inc). Suitable proteases that can be used in the present invention include Enzeco purified papain concentrate, Panol purified papain, Enzeco fungal acid protease, and Enzeco fungal protease 100 (EDC). Suitable hemicellulases that can be used in the present invention include Enzeco hemicellulase 20M (EDC); Hemicellulase Amano 90 (Amano Enzymes USA); and Multifect XL (Danisco).

The bioactive coating can include an optional pH-modifying component that is used to adjust the pH to a range of about 2 to about 7, and preferably a range of about 3 to about 7 that is effective in activating the enzyme component and maximizing enzymatic activity. The pH-modifying component generally includes an acidulant, a basic agent, a buffering agent, a salt, or any combinations thereof that are effective to modify the pH of an aqueous composition and activate the enzyme component of the bioactive composition. The optional pH-modifying component can be included as part of the bioactive composition or the binder. Alternatively, a pH-modifying component can be added to the aqueous composition to bring the pH to the desired range of about 3 to about 7 prior to, during or after immersion of the coated raw vegetables.

Some non-exhaustive examples of ingredients that can be used to form the pH-modifying component include organic acids, such as acetic acid, gluconic acid, tartaric acid, malic acid, ascorbic acid, fumaric acid, succinic acid, citric acid, or the like; phosphoric acid; buffering agents of such organic acids, such as calcium citrate, ferrous gluconate, ferrous citrate, calcium acetate, magnesium acetate, zinc citrate, zinc gluconate, calcium maleate, calcium succinate, sodium acetate, sodium maleate, sodium succinate, iron fumarate, sodium citrate, or the like; and/or any combinations thereof. Basic compounds like sodium hydroxide or the like may also be included as part of the pH-modifying component in the present invention.

When the pH-modifying component is added to the bioactive composition or the binder to form the bioactive coating, the concentration of the pH-modifying component varies depending on the materials used to form the pH-modifying component and the amount of the aqueous composition that will be used during enzymatic processing. Combinations of weak organic acids and their corresponding salts are used to form the pH-modifying component when the goal is to provide a pH buffered system that stays within a particular range. For example, if a goal is to maintain a buffered pH environment that stays within a range of about 4 to about 6, then a 60:40 blend of citric acid:sodium citrate is effective to produce this pH range. This translates into 0.30 weight percent citric acid and 0.20 weight percent sodium citrate, based on the total weight of the raw whole vegetable when the coated vegetable:water ratio is 1:3. The pH-modifying component can be encapsulated if needed to prevent premature deactivation of the enzymes during the coating process or during storage when practicing the present invention. In one embodiment, a sufficient amount of an acidulant, such as citric acid and salt, such as calcium citrate is used to deliver dietary calcium and maintain the pH at a range of about 2 to about 6. Maintaining a pH of less than about 7, and preferably, less than about 6 during enzymatic and/or conventional processing is important to avoid undesired degradation, hydrolysis and/or modification of the protein, carbohydrate and/or fat portion of raw vegetables. Hence, the use of a combined buffer system involving calcium citrate is one way to deliver dietary calcium while avoiding nutritional losses in the form of degradation at pH conditions of more than 7.5.

The bioactive coating typically includes an emulsifier component, particularly when an oil-based binder is used and/or when oleaginous legumes or raw vegetables having an appreciable lipid content are to be coated and subsequently enzyme degraded in accordance with the present invention. It has been discovered that including the emulsifier component helps to release the enzyme component from the oil-based binder so that the enzymes are capable of functioning more effectively in the aqueous composition. In addition, the presence of an emulsifier component is also important in helping to eliminate raffinose, stachyose and verbascose in oleaginous legumes and/or raw vegetables with an appreciable lipid content. Some non-exhaustive examples of suitable emulsifiers include lecithin, organic lecithin, deoiled lecithin, polysorbate 60, polysorbate 80, propylene glycol, sodium dioctylsulfosuccinate, mono-glycerides, distilled mono-glycerides, di-glycerides, distilled di-glycerides, sodium lauryl sulfate, lactylic esters of fatty acids, polyglycerol esters of fatty acids, triacetin, and combinations thereof.

The emulsifier component can be added at a ratio of about 4:1 or lower (oil-based binder:emulsifier component) when an oil-based binder is used. Alternatively, the concentration of the emulsifier component can range from about 0.01 to about 10 percent by weight, based on the total weight of the raw whole vegetables when oleaginous legumes and/or raw whole vegetables with appreciate lipid content are being used. The emulsifier component may be included as part of the binder or as part of the bioactive composition in liquid, liquefied, melted, molten, solid, or in granular form. Suitable emulsifiers for use in the present invention include organic lecithin from Clarkson Soy Products (Ill.) and Solec™ 8160 from the Solae Company (St. Louis, Mo.).

The bioactive composition and/or binder may include additives in the form of maltodextrins that function to (1) aid dispersion of powders (2) prevent caking. In the present invention, a hygroscopic maltodextrin can be included to help bind excess moisture or liquid during the coating process or during extended storage of the bioactive raw vegetables so that premature enzyme degradation or inactivation is avoided. If a maltodextrin is used in the present invention the concentration can range from about 0.01 weight percent to about 9.7 weight percent, based on the total weight of the raw whole vegetable. Suitable examples of maltodextrins for use in the present invention include Star Dri® 100 Maltodextrin from Tate and Lyle (Decatur, Ill.).

As noted in U.S. application Ser. No. 11/881,539 and International Application PCT/IB2008/001659, other additives that influence coating conditions and/or nutritionally enhance the final vegetable products may also be included as part of the bioactive composition and/or the binder. They include enzyme catalysts, natural and/or artificial flavors; artificial colors; naturally-occurring pigments, such as, for example, chlorophyll, anthocyanin, betalain, betaine, carotenoid, anthoxanthins; herbs; spices; vitamins, such as Vitamin B1 (thiamin), Vitamin B2 (Riboflavin), Vitamin B3, Vitamin B6, vitamin B12 (cyanocobalamin), Pantothemic acid, niacin, thiamin, Vitamin A, Vitamin D, Vitamin E, Vitamin C, Folic Acid, and Biotin; minerals, such as calcium, iron, zinc, copper, selenium, magnesium, manganese; plant extracts; essential oils; sugars such as sucrose, fructose, glucose, or maltose; preservatives; antioxidants; any additive that improves the aqueous enzyme composition application to, uptake by, or subsequent processing of the raw whole vegetable; or any combination of any of these. Additives, such as vitamins, minerals and other bioactive ingredients that are sensitive to water, acidity, light and oxygen may be encapsulated prior to inclusion in the bioactive composition or binder when practicing the present invention to prevent premature destruction. These additives may be included so long as (1) premature activation of any enzymes is avoided and/or (2) premature destruction of the nutritional profile and/or undesirable modification of the raw whole vegetable are avoided. In one example, oil-soluble vitamins (vitamin A and/or E) are added to a lipid binder that is used during the coating process. In another example, calcium citrate is added to a water-based binder that is used during the coating process. As noted in U.S. application Ser. No. 11/881,539 and International Application PCT/IB2008/001659, the bioactive composition may include (1) an enzyme component only and/or (2) may optionally include a pH-modifying component, an emulsifier component and other additional ingredients that aid the coating process and/or modify the chemical and nutritional properties of the raw whole vegetables when practicing the present invention. In an alternate embodiment, the bioactive composition contains at least one vitamin and/or mineral in the form of a pH—modifying component without the addition of an exogenous enzyme. In this embodiment, the bioactive component is applied to the surface of the raw whole vegetable to form a nutritionally enriched or enhanced bioactive raw vegetable. In one example, the bioactive composition includes calcium citrate at an amount that is sufficient to deliver at least 5%, at least 10%, at least 15%, at least 20%, at least 25%, at least 30%, at least 40%, at least 50%, at least 60%, at least 70%, at least 80% and/or at least 90% of the RDI for calcium. In another example, the bioactive composition includes ferrous gluconate at an amount that is sufficient to deliver at least 5%, at least 10%, at least 15%, at least 20%, at least 25%, at least 30%, at least 40%, at least 50%, at least 60%, at least 70%, at least 80% and/or at least 90% of the RDI for iron. In a third example, the bioactive composition includes zinc citrate at an amount that is sufficient to deliver at least 5%, at least 10%, at least 15%, at least 20%, at least 25%, at least 30%, at least 40%, at least 50%, at least 60%, at least 70%, at least 80% and/or at least 90% of the RDI for zinc.

In another example, ferrous gluconate at a concentration of 0.30 to 0.35 weight percent may be used as the bioactive composition so that delivery of at least 50% of the RDI for iron is possible while 2% calcium citrate is used to coat raw pinto beans so that delivery of at least 10% of the RDI for calcium is possible. In another embodiment, the bioactive composition includes an acidulant in the form of a citric acid and a salt in the form of a calcium citrate which is used to deliver at least 5% of the RDI for calcium. In a third embodiment, gluconic acid and ferrous gluconate is included as part of the binder or bioactive composition and is effective to deliver dietary iron while helping to maintain the pH to a range of about 3 to about 6.

The binder may be applied to the raw vegetable compositions separately from the bioactive composition or mixed with the bioactive composition to form as slurry that is coated onto the raw vegetables. The coating or application method used in the present invention should be performed under temperature, agitation and pressure conditions that (1) ensure a substantially uniform bioactive coating, (2) do not result in premature deactivation or destruction of the bioactivity of the coating, (3) do not undesirably modify (shrivel, etc) the seed coat/top surface of the raw vegetables, (4) is gentle enough to avoid breaking, shattering or chipping the raw whole vegetables and /or (5) does not promote undesirable nutritional and /or organoleptic changes to the raw whole vegetables during conventional processing and/or prior to consumption.

In general, a 1-stage coater, 2-stage coater, a standard tablet coating pan, or a fluidized bed coater may be used to coat raw whole vegetables of the present invention when the binder is to applied separately from the bioactive composition or when both the binder and bioactive composition are mixed to form a slurry. A suitable example of coating equipment includes Master Series two-stage liquid & powder coating system that is available from Spray Dynamics (St. Louis, Mo.). The bioactive composition and/or binder, either separately or combined can also be applied by immersing, spraying, spray coating, or by forming a thin film of the bioactive coating on the vegetables. The coating thickness typically ranges from about 2 microns to about 2 millimeters depending on the amount of coating applied and is also preferably substantially uniform in thickness.

After applying the coating, the coated vegetables are dried to reduce surface moisture and tackiness of the coated product. During the coating process, normal conditions in the spray coater (rotating drum) are such that the coated raw vegetables are dried by the time they exit the rotating drum. Similarly, when an oil-based binder is used, the temperature and air conditions in the coater are such that the binder is cured, hardened and/or solidified prior to exiting the drum. In the rare cases where the binder is still fluid or wet, a separate dryer may be used to dry the coated product. In general, any dryer that is suitable for use in drying particulate matter can be used to dry the coated vegetables in the present invention as long as the time, temperature, airflow and/or agitation conditions do not deactivate or remove the bioactive coating. As an example, forced air dryer may be used to dry the coated vegetables. After drying, the enzyme-coated raw whole vegetables can be conventionally packaged and distributed or immediately exposed to appropriate water, pH and temperature conditions that promote enzymatic degradation.

It is noted that the present invention results in the incorporation of exogenous enzymes and/or vitamins/minerals into a coating located on the surface of raw whole vegetables such that the enzymes remain active after coating to facilitate enzymatic degradation of oligosaccharide sugars when the coated raw vegetables are placed in suitable water, temperature and pH conditions. As used herein, the term "exogenous enzymes" refers to the addition of an external source of enzymes. The benefits of forming bioactive raw vegetables that contain a bioactive coating includes (1) ease of preparation, (2) potentially lower cooking times, and/or (3) simple delivery of key nutrients in a plant-based matrix, such as calcium and iron. Given how easy it is to deactivate enzymes along with potential dust/allergy concerns when working with granular compositions, bioactive coatings offer an alternative to obtaining more easily digestible and/or nutritionally enriched plant foods without the technical challenges encountered in making sure the enzymes work. In addition, unlike microbial compositions that are more robust than free enzymes and readily bounce back due to the high ($10^5$ to $10^7$ cells/ml) application rates after processing conditions, enzymes are much more difficult to use during food processing and therefore, embedding enzymes in a binder that adheres the enzymes to raw whole vegetable further simplifies their use in the food industry or by a consumer. In addition, other benefits can be derived depending on the ingredients used to form the bioactive composition.

As noted above, the bioactive composition can include one or more enzymes that are not activated or un-activated during the coating process. Active enzymes during the coating process will (1) start undesired enzyme activity, (2) exhaust all enzyme activity during coating, and/or (3) not allow for enzyme degradation once the coated beans are placed in optimal conditions that allow the enzyme to function. Hence the inclusion of activated or enzymes promoting active enzymatic modification during the coating process is preferably avoided. Therefore, coating raw legumes or other raw vegetables with an un-activated bioactive composition is preferred when practicing the present invention. Thereafter, activation upon soaking or placing in optimal time, temperature, solvent and pH conditions can be performed to promote enzymatic activity on the raw whole vegetables as has been disclosed in U.S. Pat. No. 6,033,692 for example.

The present invention is more particularly described in the following examples that are intended as illustrations only since numerous modifications and variations within the scope of the present invention will be apparent to those skilled in the art.

EXAMPLES

Example 1

2000 lbs of cleaned dried pinto beans were coated with two different versions of Vegizyme™ that was formulated to remove up to 100% of raffinose, verbascose and stachyose in raw whole beans using a 2-stage coater. The two different versions of Vegizyme™ (bioactive composition) were prepared based on the following composition (weight percent is based on raw bean feed rate):

TABLE 1

| Ingredient | Vegizyme (1) wt % | Vegizyme (2) wt % |
|---|---|---|
| Food grade enzymes | 20 | 5 |
| Citric acid | 30 | 7.5 |
| Sodium citrate | 20 | 5 |
| Maltodextrin (StarDri 100) | 20 | 82.5 |

The operating conditions are as follows:

TABLE 2

| Process/Operating Conditions | #1 | #2 | #3 | #4 | #5 | #6 | #7 |
|---|---|---|---|---|---|---|---|
| Raw bean feed rate (lbs/hr) | 250 | 250 | 250 | 250 | 250 | 250 | 250 |
| Raw bean temperature (F.) | 70 | 70 | 70 | 70 | 70 | 70 | 70 |
| Binder Type* | NT | NT | NT | NT | NT | NT | NT |
| Binder Temperature (F.) | 120 | 120 | 120 | 120 | 120 | 120 | 120 |
| Binder application rate (wt %)** | 0.5 | 0.5 | 1.0 | 1.0 | 2.0 | 2.0 | 2.0 |
| Plant room temperature (F.) | 70 | 70 | 70 | 70 | 70 | 70 | 70 |
| Vegizyme ™ Formula*** | 1 | 1 | 1 | 1 | 2 | 2 | 2 |
| Vegizyme ™ concentration (wt %) | 1 | 1 | 1 | 1 | 1 | 1 | 1 |

*refers to binder type - NT stands N-Tack (National Starch and Chemical Company)
**refers to binder application rate is in weight percent based on raw bean feed rate
***Vegizyme ™ Formula (1) or (2) was used for each variable Coated beans from #1-#4 were dry by the time the beans exited from the rotating drum of the 2-stage coater. Coated beans from #5-#7 were too sticky and required additional drying. 300 grams of each type of coated beans were each subsequently immersed in 900 grams of water, with agitation, at temperatures of about 100° F. to about 120° F. The initial pH values for the seven immersed bean samples ranged from 4 to about 5. Sugars analysis revealed that over 90% of raffmose and stachyose sugars were eliminated by the Vegizyme-based coating.

Example 2

2000 lbs of cleaned dried pinto and great northern beans were coated with various Vegizyme™ formulas that were formulated to remove up to 100% of raffinose, verbascose and stachyose in raw whole beans using a 2-stage coater. In addition, some the formulas contained iron, calcium and a blend of 12 vitamins and minerals. The different versions of Vegizyme™ (bioactive composition) were prepared based on the following composition (in weight percent based on raw bean feed rate):

TABLE 3

| Ingredients | #1 | #2 | #3 | #4 | #5 | #6 | #7 | #8 | #9 | #10 |
|---|---|---|---|---|---|---|---|---|---|---|
| Cellulase AP10[1] | 0.025 | 0.025 | 0.025 | 0.025 | 0.025 | 0.025 | 0.025 | 0.025 | 0 | 0 |
| Pectinase P-10[1] | 0.045 | 0.045 | 0.045 | 0.045 | 0.045 | 0.045 | 0.045 | 0.045 | 0 | 0 |
| Hemicellulase 20M[2] | 0.045 | 0.045 | 0.045 | 0.045 | 0.045 | 0.045 | 0.045 | 0.045 | 0 | 0 |
| Papain[1] | 0.045 | 0.045 | 0.045 | 0.045 | 0.045 | 0.045 | 0.045 | 0.045 | 0 | 0 |
| α-galactosidase[1] | 0.045 | 0.045 | 0.045 | 0.045 | 0.045 | 0.045 | 0.045 | 0.045 | 0 | 0 |
| α-amylase[1] | 0.125 | 0.125 | 0.125 | 0.125 | 0.125 | 0.125 | 0.125 | 0.125 | 0 | 0 |
| Citric Acid[3] | 0.30 | 0.23 | 0.34 | 0.34 | 0.30 | 0.35 | 0.37 | 0.20 | 0 | 0 |
| Sodium Citrate[3] | 0.20 | 0.11 | 0.00 | 0.00 | 0.07 | 0.00 | 0.00 | 0.00 | 0 | 0 |
| StarDri100[3] | 0.17 | 0.00 | 0.00 | 0.00 | 0.00 | 0.00 | 0.00 | 0.00 | 0 | 0 |
| Ferrous gluconate[5] | 0.00 | 0.33 | 0.33 | 0.00 | 0.00 | 0.34 | 0.00 | 0.00 | 0.33 | 0 |
| Calcium citrate[3] | 0.00 | 0.00 | 1.00 | 0.00 | 0.00 | 0.00 | 1.00 | 0.00 | 0 | 2.00 |
| Vit./Min Blend[4] | 0.00 | 0.00 | 0.00 | 0.33 | 0.00 | 0.00 | 0.00 | 0.33 | 0 | 0 |
| Lecithin | 0.00 | 0.00 | 0.00 | 0.00 | 0.30 | 0.50 | 0.30 | 0.30 | 0 | 0 |
| Total % | 1.00 | 1.00 | 2.00 | 1.00 | 1.00 | 1.50 | 2.00 | 1.16 | 0.33 | 2.00 |

[1] obtained from Amano;

[2] obtained from Enzyme Dev. Corp;

[3] obtained from Tate &Lyle (ADM) and

[4] obtained from Fortitech (Product Code FT062881) (NY);

[5] obtained from Purac America Inc. (GA).

The operating conditions were as follows:

TABLE 4

| Process/Operating Conditions | #1 | #2 | #3 | #4 | #5 | #6 | #7 |
|---|---|---|---|---|---|---|---|
| Raw bean feed rate (lbs/hr) | 250 | 250 | 250 | 250 | 250 | 250 | 250 |
| Raw bean temperature (F.) | 70 | 70 | 70 | 70 | 70 | 70 | 70 |
| Binder Type* | NT | NT | NT | NT | NW | NW | NW |
| Binder Temperature (F.) | 120 | 120 | 120 | 120 | 120 | 120 | 120 |
| Binder application rate (wt %)** | 0.5 | 0.5 | 0.5 | 0.5 | 0.5 | 1.0 | 1.0 |
| Plant room temperature (F.) | 70 | 70 | 70 | 70 | 70 | 70 | 70 |
| Vegizyme ™ Formula*** | 1 | 2 | 3 | 4 | 5 | 7 | 8 |
| Vegizyme ™ concentration (wt %) | 1.00 | 1.00 | 2.00 | 1.00 | 1.00 | 2.00 | 1.16 |

*refers to binder type - NT stands N-Tack (National Starch and Chemical Company) while NW is Naturewax from Cargill (MN).
**refers to binder application rate is in weight percent based on raw bean feed rate.
***Vegizyme ™ Formulas (#1-5, 7-8 from Table 3)

Experiments #1-#7 all produced bioactive raw coated beans that were substantially coated with bioactive compositions. 300 grams of each type of coated beans were each subsequently immersed, with agitation, in 900 grams of water at temperatures of about 100° F. to about 130° F. The initial pH values for the immersed bean samples ranged from 4 to about 5. Sugars analysis indicated that over 90% of raffinose and stachyose sugars were eliminated by the bioactive coating. Experiments #8 through #10 produced bioactive raw coated beans that were substantially coated with bioactive compositions. 100, 200 and 300 grams samples of each type of coated bean from Experiments #8 through #10 were each subsequently immersed, with agitation, in 900 grams of water at temperatures of about 100° F. to about 130° F. The initial pH values for the immersed bean samples ranged from about 2 to about 6.5. Calcium, iron and zinc analysis indicated that at least 5% of the vitamin and/or mineral were absorbed into the raw beans after soaking for a minimum of 30 minutes.

Although the present invention has been described with reference to preferred embodiments, workers skilled in the art will recognize that changes may be made in form and detail without departing from the spirit and scope of the invention.

What is claimed is:

1. A method of forming a bioactive coated raw legume comprising:
    applying a liquid binder at a temperature of about 90° F. to about 140° F., wherein the binder is an oil-based binder to a raw legume to form a sticky raw legume; and
    applying a granular bioactive composition comprising at least one enzyme that is substantially free of microorganisms to the sticky raw legume to form the bioactive coated raw legume.

2. The method of claim 1 and further including drying the bioactive coated raw legume.

3. The method of claim 1 wherein the bioactive composition further comprises a buffer that includes an acidulant and a salt of the acidulant.

4. The method of claim 1 wherein the legume is large white or Great Northern, small white, pinto, red kidney, black, calico, pink cranberry, red mexican, brown, bayo, lima, navy, smooth and wrinkled peas and yellow or green varieties, black eye beans, cowpeas, purple hull peas, cream peas, crowder peas, field peas, garbanzo beans and chick peas, soybeans, red beans, yellow-eye beans, azuki beans, mung beans, tepary beans, fava beans, pulses, or any combination of any of these.

5. The method of claim 1 wherein the binder is applied at a concentration of less than 5 weight percent, based on the total weight of the raw legume.

6. The method of claim 1 and further comprising immersing the bioactive coated raw legume in water at a temperature of about 90° F. to about 150° F., wherein the enzymes are effective to degrade the raw legume.

7. The method of claim 1 wherein the bioactive composition is encapsulated.

8. The method of claim 1 wherein the enzymes are effective to degrade carbohydrates in the raw legume.

9. The method of claim 1 wherein the bioactive composition is a cellulase, a hemicellulase, a pectinase, a protease, an amylase, an alpha-galactosidase, citric acid, calcium citrate, sodium citrate or any combination of any of these.

10. A method of forming a bioactive coated raw legume comprising:
    coating a raw whole legume with a slurry comprising a binder at a temperature of about 90° F. to about 140° F., and a bioactive composition to form a slurry-coated raw legume, the bioactive composition comprising at least one enzyme that is substantially free of microorganisms and effective to degrade raffinose, stachyose, verbascose or any combination any of these; and
    curing the slurry to form the bioactive coated raw legume.

11. The method of claim 10 wherein the binder comprises partially hydrogenated palm kernel, soybean, cottonseed, corn, canola, peanut, palm, babassu, sunflower, and/or safflower oils, fully hydrogenated palm kernel, canola, soybean, cottonseed oil, blends of partially hydrogenated and fully hydrogenated palm kernel, soybean, canola, cottonseed, corn, peanut, palm, babassu, sunflower, and/or safflower oils, mono-, di- and triglycerides; food-grade paraffin-based waxes, food-grade petroleum waxes, carnuba wax, bran wax, tallow, shellac, beeswax, or any combination of any of these.

12. The method of claim 10 and further comprising soaking the bioactive coated raw legume in water at temperature of about 90° F. to about 150° F., wherein the enzymes are effective to degrade the raw legume.

13. The method of claim 10 wherein curing comprises drying, solidifying, or any combination of any of these.

14. The method of claim 10 wherein the bioactive composition comprises:
    enzymes comprising cellulase, hemicellulase, pectinase, protease, alpha-galactosidase or any combination of any of these;
    an emulsifier comprising lecithin; and
    a pH-modifying component comprising organic acid.

15. The method of claim 10 wherein the bioactive composition comprises:
    enzymes comprising cellulase, hemicellulase, pectinase, protease, amylase, alpha-galactosidase or any combination of any of these; and
    a pH-modifying component comprising citric acid, calcium citrate and sodium citrate.

16. A bioactive coated raw legume comprising:
a raw whole legume having a moisture content of less than about 40 weight percent, based on the total weight of the legume;
a binder coated onto the raw legume, wherein the binder has a concentration of more than about 0.01 weight percent, based on a total weight of the raw legume; and
a bioactive composition mixed with the binder, the bioactive composition comprising at least one encapsulated enzyme that is substantially free of microorganisms and that is effective to degrade the raw legume, raffinose, stachyose, verbascose or any combination of any of these, the bioactive composition having a concentration of at least about 0.01% weight percent, based on the total weight of the raw legume.

17. The bioactive coated raw legume of claim 16 wherein the bioactive composition comprises:
enzymes comprising cellulase, hemicellulase, pectinase, protease, amylase, alpha-galactosidase or any combination of any of these;
an emulsifier comprising lecithin; and
a buffer comprising citric acid and sodium citrate.

18. The bioactive coated raw legume of claim 16 wherein the binder is an oil-based binder and the binder has a melting point of more than about 90° F.

19. A method of forming a bioactive coated raw legume comprising:
applying a liquid binder to a raw legume to form a sticky raw legume; and
applying a granular bioactive composition comprising at least one vitamin or mineral to the sticky raw legume to form the bioactive coated raw legume.

20. The method of claim 19 wherein the bioactive composition is effective to maintain a pH of about 2 to about 7.

21. The method of claim 19 wherein the bioactive composition comprises calcium citrate and is effective to deliver at least about 5% of the RDI of calcium in a 100 gram sample of coated legumes.

* * * * *